United States Patent [19]
Holler

[11] Patent Number: 4,760,841
[45] Date of Patent: Aug. 2, 1988

[54] METHOD AND APPARATUS FOR LOWER BACK MANIPULATION

[76] Inventor: H. Stanford Holler, General Delivery, Unionville, Pa. 19375

[21] Appl. No.: 33,143

[22] Filed: Apr. 1, 1987

[51] Int. Cl.[4] .......... A61H 1/00; A61F 5/00

[52] U.S. Cl. .......... 128/52; 128/70; 128/33

[58] Field of Search .......... 128/52, 51, 44, 70, 128/33

[56] References Cited

U.S. PATENT DOCUMENTS

| | | | |
|---|---|---|---|
| 2,534,587 | 12/1950 | Fisher et al. | 128/71 |
| 2,548,408 | 4/1951 | Tammen | 128/52 |
| 2,666,429 | 1/1954 | Alexander et al. | 128/33 |
| 2,781,040 | 2/1957 | Hill | 128/33 |
| 2,856,917 | 10/1958 | Mack | 128/33 |
| 2,949,911 | 8/1960 | Kennard et al. | 128/25 |
| 3,003,497 | 10/1961 | Nunes | 128/33 |
| 3,238,936 | 3/1966 | Siedentop | 128/24.3 |
| 3,585,989 | 6/1971 | Little | 128/33 |
| 3,830,233 | 8/1974 | Hill | 128/52 |
| 3,882,856 | 5/1975 | Heuser et al. | 128/52 |
| 4,230,098 | 10/1980 | Uematsu | 128/33 |
| 4,458,675 | 7/1984 | Nakao et al. | 128/52 |

OTHER PUBLICATIONS

Advertisement for Kyroflex-Kyro Manufacturing Co.
Advertisement for Anatomotor-Hill Laboratories Company.
Advertisement for Spinalator.
Advertisement for Combi Series-LIC Care, Inc.
Advertisement for Panasonic Shiatsu.

*Primary Examiner*—Edgar S. Burr
*Assistant Examiner*—Tonya Lamb
*Attorney, Agent, or Firm*—Seidel, Gonda, Goldhammer & Abbott

[57] ABSTRACT

A method and apparatus for passively mobilizing the joints in the lower back, the sacroiliac and the lumbosacral and lower lumber intervertebral joints by simultaneously manipulating the pelvis in an oppositely directed reciprocating motion while also inducing small movements over a period of time to the joints of the lumbosacral spine in a timed relationship with the reciprocating motion of the pelvis without twisting and without forceful contact or manipulation of these regions.

15 Claims, 3 Drawing Sheets

METHOD AND APPARATUS FOR LOWER BACK MANIPULATION

BRIEF SUMMARY OF THE INVENTION

This invention relates to a method of and apparatus for manipulating and for passively mobilizing the joints of the lower back, the sacroiliac, and the lumbosacral and lower lumbar intervertebral joints. The present invention relates to simultaneously manipulating the joints of the lumbosacral spine and pelvis by a series of small movements over a period of time without twisting and without forceful contact or manipulation. The present invention also relates to effectuation of the normal alignment of the ilia (hips), sacrum and lower lumbar vertebrae and to restore normal, pain free movement in this area.

BACKGROUND OF THE INVENTION

There are a number of known apparatus for the exercise and movement of the body portions by using reciprocating boards or cushions on various portions of the body or which include cushions which move in various directions across portions of the body. See generally the U.S. Pat. Nos. 3,585,989, Little, 2,949,911, Kenard et al, 2,666,429, Alexander et al, and 2,856,917, Mac. Additionally there is found a number of devices which utilize rollers on various portions of the body and the spine in order to perform a muscle massage. See generally the U.S. Pat Nos. 3,830,233, Hill, 3,238,936, Seidentop and 4,230,098, Uematsu. Many of these devices operate in conjunction with traction means for relieving pressure on the vertebrae during movement of the various portions of these devices.

SUMMARY OF THE INVENTION

The present invention relates to a method and apparatus for simultaneously manipulating the joints of the lumbosacral spine and pelvis through contact and movement of certain portions of this region of the body by a controlled reciprocating motion at a number of specifically defined contact positions.

The apparatus as contemplated by the present invention comprises two pelvic carriages, which are positioned adjacent to one another and support the opposite sides of the buttocks when a person is lying down. The two pelvic carriages are adapted to reciprocate in opposite directions during manipulation. The apparatus also comprises a roller carriage for simultaneously reciprocating and contacting the lumbosacral spine on at least two defined positions in a specific movement relationship with the two pelvic carriages. The roller carriage is positioned to contact the back and reciprocate along the lumbosacral spine when the person is lying down. It is contemplated that the relative speed of manipulation of the pelvic carriages and roller carriage may be adjusted as well as their direction of manipulation relative to each other may be varied. Also realignment of the contact positions on the lumbosacral spine with respect to the center line of the spinal column by the roller carriage may be varied.

One preferred series of manipulations as contemplated by the present invention includes the movement of both cheeks of the buttocks in an opposite reciprocating motion with a series of small movements such that one side never passes the other in the pelvic area. Simultaneously, while applying the reciprocating motion to the pelvic region, contact is being made in an offset or staggered and asymmetrical relationship adjacent the center line of the lumbosacral spine. This contact by the roller carriage along the lower spine is reciprocated in a timed relationship with respect to the pelvic carriage movement.

In one mode, the pelvic carriages oscillate in opposite directions with respect to one another with the relative right pelvic carriage moving first towards the feet (footward) and the relative left roller carriage moving towards the head of the person lying on the apparatus (headward). The roller carriage simultaneously reciprocates along the lower spine with its initial movement being also towards the feet. The speed of the roller carriage is preferably twice that of the pelvic carriages with the overall distance of travel of the roller carriage being twice that of the pelvic carriages. Two rollers on the roller carriage are positioned in a generally offset relationship and are staggered and asymmetrical with respect to the center line of the spine. The first or relatively lower roller is positioned footward of the second roller and close to the mid-line of the spine. This footward roller passes inside of the ilium or hip and strikes the posterior aspect of the sacrum on one side. The second roller is offset from the center line and positioned headward so that it will not strike the sacrum in its most footward travel.

In alternate embodiments the relative movement of the pelvic carriages with respect to one another and with respect to the roller carriage can be varied so as to effectuate different manipulations. Additionally, the relative positioning of the two rollers on the roller carriage may also be altered so as to further effect a varied manipulation.

Further advantages of the invention will be understood by describing a preferred embodiment as shown in the drawings. For the purpose of illustrating the invention, there is shown in the drawings a form which is presently preferred; it being understood, however, that this invention is not limited to the precise arrangements and instrumentalities shown.

DETAILED DESCRIPTION OF THE DRAWINGS

Figure 1:
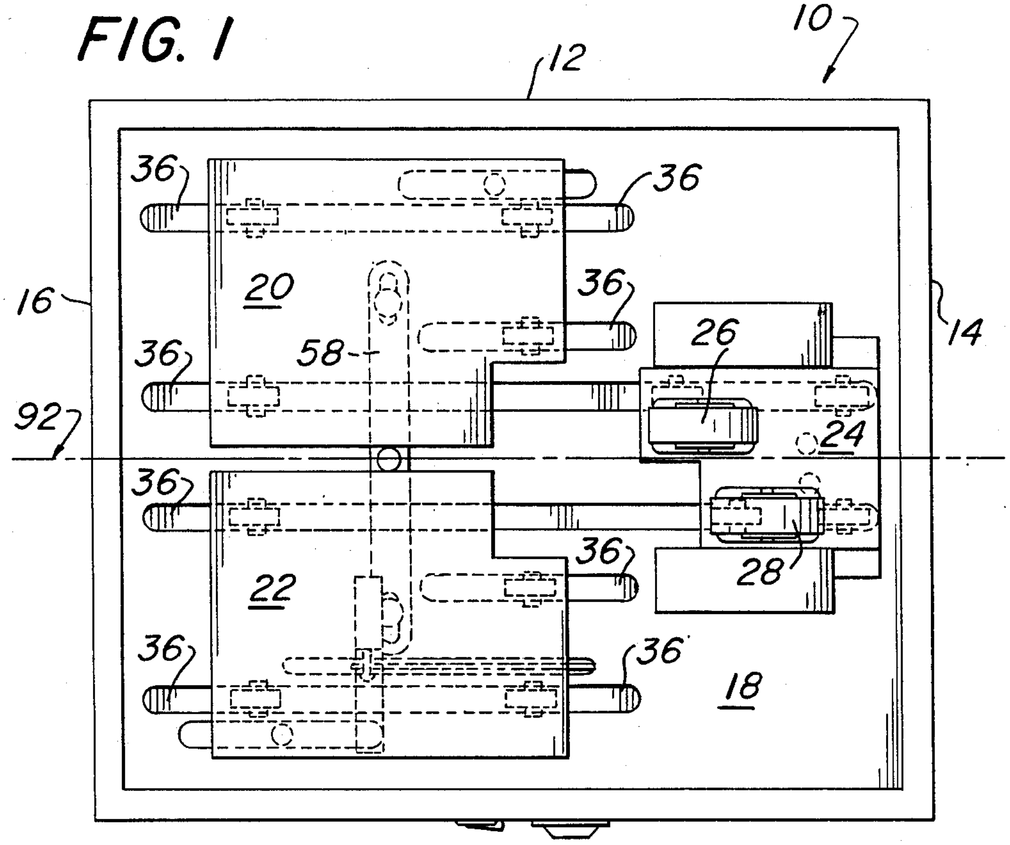
FIG. 1 shows a top plan view of an apparatus contemplated for use as part of the present invention.

In the drawings where like numerals indicate like elements there is shown an apparatus 10 of the present invention for passively mobilizing the joints of the lower back, the sacroiliac, and the lumbosacral and lower lumbar intervertebral joints. The appratus 10 as shown in FIG. 1 generally comprises a housing 12 having front or forward end 14 and rear or lower end 16. As shown in FIG. 1 the top 18 of the housing 12 supports a number of elements which are adapted for a reciprocating motion across this upper surface 18. The reciprocating elements generally include two pelvic carriages 20 and 22 and a roller carriage 24. The roller carriage 24 as shown includes two rollers 26 and 28 which project upward from the top surface of the roller carriage 24.

Figure 2:
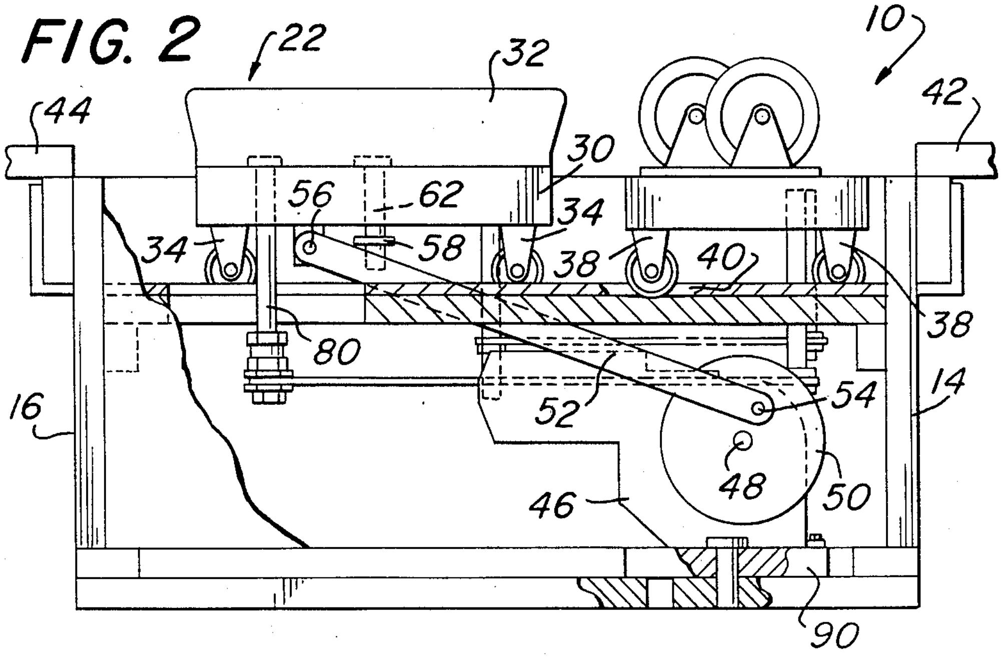
FIG. 2 shows a partial cross sectional view of the apparatus illustrated in FIG. 1.

As can be seen in FIG. 2 each pelvic carriage 20, 22 generally include a carriage body 30, an upper padded portion 32 and a series of support casters 34. The pelvic carriage casters 34 are generally supported within the top 18 of the housing 12 by means of caster guides 36. The caster guides 36 may take the form of slots in the top surface 18 of the housing 12 and, preferably, prevent movement of the pelvic carriages 20, 22 in a lateral direction. The caster guides 36 permit the casters 34 and their corresponding pelvic carriages 20, 22 to move freely within the guides 36 both towards the forward 14 end of the housing 12 and the rear end 16 of the housing 12.

Roller carriage 24 also has a series of casters 38 which support the roller carriage 24 on the top surface 18 of the housing 12. The casters 38 of the roller carriage 24 are also retained within caster guides 40 on the top surface 18 of the housing 12. The roller carriage 24 is also free to move forward and back within the caster guides 40 with the caster guides 40 preventing lateral movement of the roller carriage 24.

The apparatus 10 of the present invention performs the desired manipulation of the lower back of a person positioned on the apparatus with the right and left sides of the buttocks supported on the pelvic carriages 20 and 22, respectively. The person lies across the apparatus 10 with the rollers 26 and 28 projecting into the lower back region (proper positioning to be explained below.) The person would lie across the apparatus 10 while preferably utilizing table supports 42 and 44 which are partially shown in FIG. 2. Table support 42 is supported on the front end of the housing 12 so as to project forward and support the upper back and head. Table support 44 is supported on the rear end 16 of the housing 12 and projects rearward of the body and supports the legs and feet. The table supports 42 and 44 and the housing 12 completely support the body in a horizontal or supine position.

The desired manipulation of the present invention is performed by movement of the pelvic carriages 20, 22 and the roller carriage 24 in a specific relationship. Reciprocation of these portions is created through an electric motor 46 and attached linkage. Electric motor 46 includes a motor shaft 48 which is fixedly attached to a circular crank 50. A push rod or crank arm 52 is attached to crank 50 at a pivot 54. The positioning of the pivot 54 can be varied as desired to produce the proper reciprocating motion. Typically, pivot 54 is located radially from the motor shaft 48 on the surface of the crank 50. The opposite end of the crank arm 52 from its pivot attachment 54 is attached underside of pelvic carriage 22 at pivot 56. This linkage arrangement causes the reciprocation of pelvic carriage 22 through the rotation of the electric motor 46 and crank 50.

Figure 3:
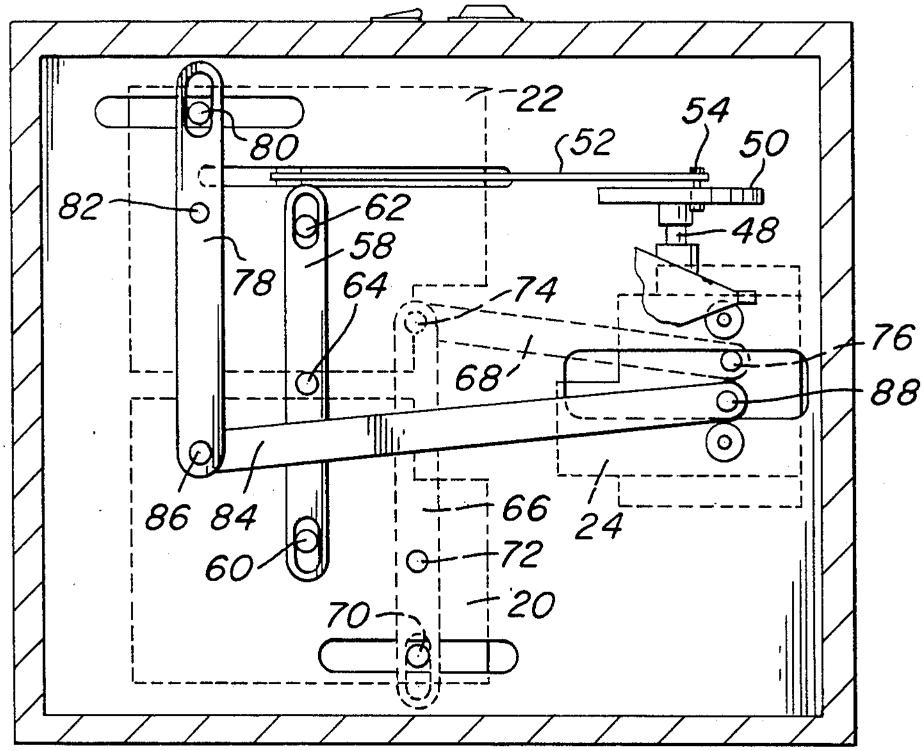
FIG. 3 is a bottom cross sectional view of the apparatus illustrated in FIG. 1.
Figure 4:
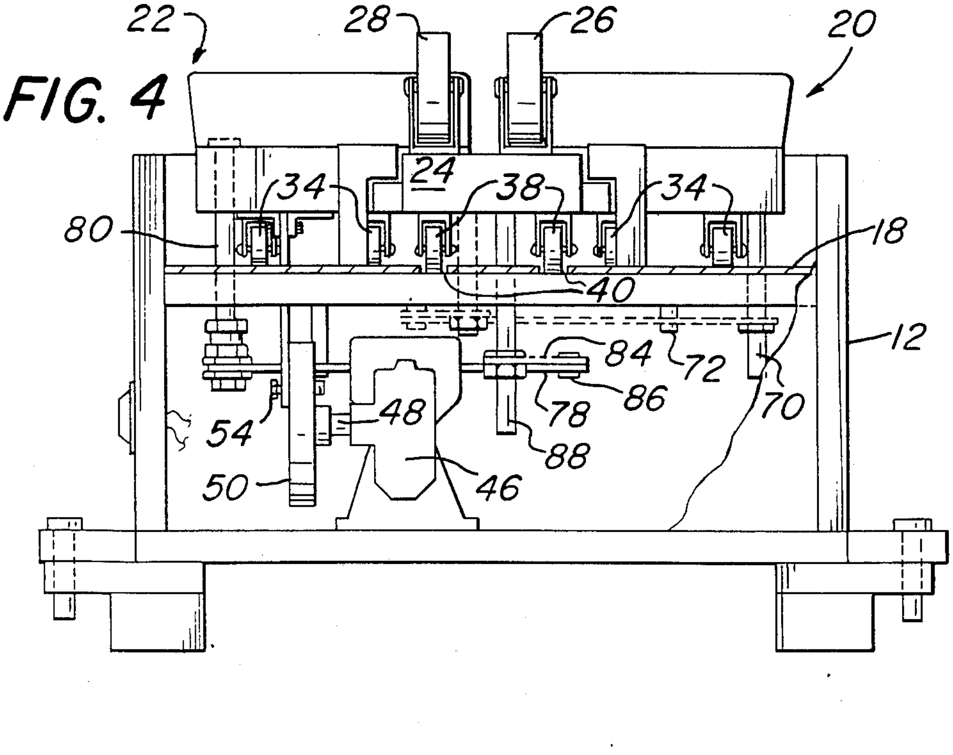
FIG. 4 is a third cross sectional view of the apparatus illustrated in FIG. 1.

It is desired that the pelvic carraiges 20 and 22 reciprocate in opposite directions with respect to one another during manipulation. Reciprocation of pelvic carriage 22 is caused by the electric motor 46 and its linkage connection through crank arm 52. As illustrated in FIG. 1 and FIG. 3 pelvic carriage 22 and 20 are attached to one another by means of a pelvic carriage link 58. Link 58 is attached to each pelvic carriage 20 and 22 at opposite ends by its engagement with studs 60 and 62 which project from the underside of the pelvic carriages 20 and 22 respectively. Studs 60, 62 are retained within a slot at opposite ends of the pelvic carriage link 58. The pelvic carriage link 58 is pivoted on housing 12 at a central position between the pelvic carriages 20, 22. This pivot 64 and its linkage connection at link 58 with the pelvic carriages 20, 22, causes an opposite reciprocation of the pelvic carriage 20 with respect the movement of carriage 22. It is preferred that the pivot 64 be positioned at the center of pelvic carriage link 58 so that the reciprocating motion of the pelvic carriages 20 and 22 is equal and opposite at all points during their motion.

Reciprocation of roller carriage 24 is perferably within a specific timed and distance relationship with respect to the movement of pelvic carriages 20 and 22. As illustrated in FIGS. 3–7 the pelvic carriages 20 or 22 may be connected by linkage to the roller carriage 24 to cause this reciprocating motion. Pelvic carriage 22 is preferably connected to roller carriage 24 by means of two link arms 78 and 84. The first link arm 78 is attached to the underside of pelvic carriage 22 by means of stud 80 which is retained within a slot in the end of first link arm 78. First link arm 78 is also pivoted on the housing 12 at a fixed pivot 82. The opposite end of the first link arm 78, from its attachment with stud 80, is secured to one end of second link arm 84 at pivot 86. Second link arm 84 is attached at its opposite end to the underside of roller carriage 24 at pivot 88.

The placement of pivot 82, which is fixed to the housing 12 and about which link arm 78 rotates, controls the relative motion of roller carriage 24 with respect to the reciprocating motion of pelvic carriage 22. Pelvic carriages 20 and 22 are moving in equal and opposite directions via link 58. The connection of pelvic carriage 22 with roller carriage 24 through link arm 78 and 84 combines to reciprocate the roller carriage 24 in the desired timed and distance relationship.

As also can be seen in FIG. 3 the reciprocating motion of roller carriage 24 may be caused by a separate linkage structure through link arms 66 and 68 (shown in phantom). Link arm 66 is attached at one end to pelvic carriage 20 via stud 70. The opposite end of link arm 66 is attached to link arm 68 at pivot 74. Link arm 68 is then connected to roller carriage 24 at pivot 76. Link arm 66 is also pivoted at 72 to the housing 12. This alternate linkage structure is used only when sliding frame 90 (discussed below) has been moved to its footward position so that the linkage will then initiate the motion of the roller carriage 24 in the same, footward, direction as that of the linkage arrangements of link arms 78 and 84. In both of these arrangements, the initial movement of the roller carriage 24 is footward. The desirability of such a relationship will be described below with reference to FIG. 7.

Figure 5:
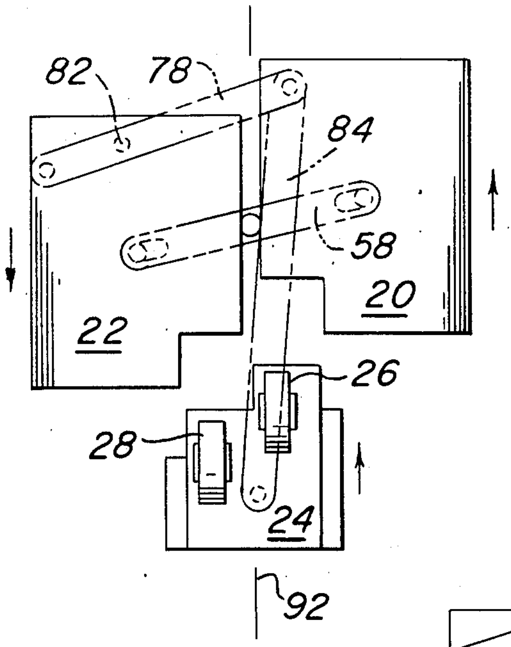
FIGS. 5, 6 and 7 are top plan views of the relative movement of the portions of the apparatus illustrated in FIGS. 1–4.
Figure 6:
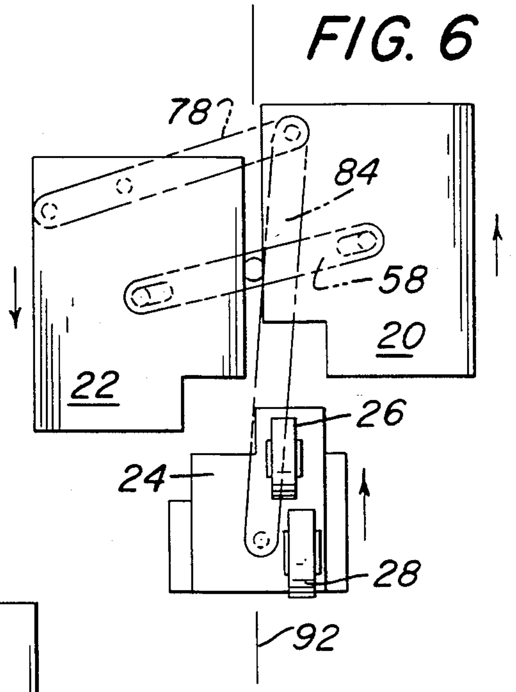
Figure 7:
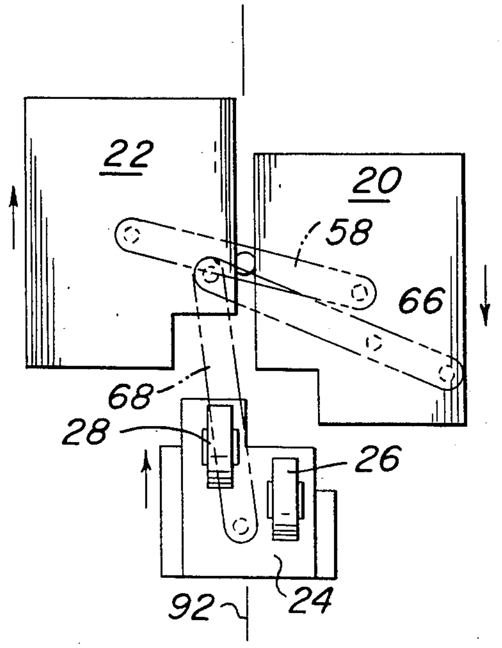

As can be seen in FIGS. 5, 6 and 7 the apparatus 10 may be adjusted to produce two different arrangements of the motion of the pelvic carriages 20, 22 with respect to the roller carriage 24. Additionally, various arrangements in the positioning of the rollers 26 and 28 on the roller carriage can be made in order to effectuate the desired type manipulation of the lower back. The movement of the elements of the apparatus 10 are specifically related to correct the alignment of the lumbar vertebrae, sacrum and ilia as desired. It is desired, however that the pelvic carriages 20 and 22 never pass one another and that their motion be limited. This is effectuated by means of link 58 which simultaneously moves the pelvic carriages 20, 22 in equal and opposite directions. In the relationship shown in the figures, the pelvic carriages move in opposite directions and then return to their side-by-side position. The return motion does then not move the opposing carriages in opposite directions of an equal throw past their initial rest position. This relationship effectively corrects the alignment of the ilia with respect to the sacrum.

FIG. 5 illustrates one preferred relationship of the movement of the elements of the apparatus 10. In this relationship the relatively left pelvic carriage 22 is first moved in the forward direction towards the front 14 of the housing 12 and towards the head of the person utilizing the apparatus 10. Likewise the opposite pelvic carriage 20 moves in the opposite direction toward the feet.

As described previously this relationship is effectuated by the rotation of the motor 46 and the crank 50. The relative motion of the pelvic carriages 20, 22 and the roller carriage 24 may be obtained, as seen in FIG. 2, by motor 46 mounted on a sliding frame 90. Moving the sliding frame 90 within the housing 12 either in the forward 14 or rearward 16 direction alters the relative relationship of the pivot 54 on crank 50 in the rest position (i.e., pelvic carriages 20, 22 side-by-side) with respect to shaft 48. For example, as shown in FIG. 2, if the crank 50 were to be rotated in a clockwise direction the initial motion of the pelvic carriage 22 would be in the forward 14 direction as illustrated in FIG. 5. However, if the sliding frame 90 were to be moved footward of its presently illustrated position towards the rear 16 of the housing 12, the pivot 54 would also be moved to a position below the rotating shaft 48 such that the initial motion of the pelvic carriage 22 would be in the rearward direction for a clockwise rotation. Thus, variations in the relative movement of the pelvic carriages 20 and 22 can be attained by adjustment of the support frame 90 in this manner.

Returning to FIG. 5, it is contemplated that the relative motion of the pelvic carriages 20 and 22 is illustrated by the arrows on opposite sides thereof. The connecting linkage as partially illustrated will cause a rearward movement of the roller carriage 24 towards the rear 16 of the housing 12. Additionally, by proper placement of pivot 82 (and its corresponding pivot 72 for pelvic carriage 20) the speed of the roller carriage can be maintained at the desired relationship with respect to the speed of the pelvic carriages 20 and 22. As illustrated in FIG. 5 the relative speed of the roller carriage is contemplated to be approximately twice that of the pelvic carriages 20, 22.

As also can be seen in FIG. 5, the relative position of the rollers 26 and 28 is in an offset or staggered and asymetrical positioning. Roller 26 is positioned footward and very close to the mid-line 92 of the apparatus and thus the center line of the spine. Roller 26 preferably moves within the groove of the back which is adjacent to the spinous processes of the spinal column. The opposite roller 28 is set at a side position and headward to the front 14 of the housing 12. This second roller 28 preferably moves up and down the muscle mass adjacent to the spinal column on the opposite side of the body or center line of the spine from roller 26. In positioning the person on the apparatus, it is desired that the first roller 26 move past medially or to the inside of the ilium or hip and strike the posterior aspect of the sacrum on one side. The person utilizing the apparatus is preferably centered on the pelvic carriages with the top of the right ilium or hip bone adjacent to the lower edge of roller 26. The opposite roller 28 is set more to the side and headward, so that it cannot strike the sacrum in its excursion footward. It is the purpose of this relationship in conjunction with the movement of the pelvic carriages 20 and 22 to aid in the manipulation of the lumbar vertebrae. The movement of the pelvic carriages 20, 22 with respect to the roller carriage 24 is specifically coordinated such that the roller carriage 24 in its footward or rearward 16 excursion moves twice the rate of speed of the footward moving pelvic carriage 20. The roller carriage catches up with the pelvic carriage at the end of its movement with the roller 26 striking the poterior aspect of the sacrum to effectively correct the sacroiliac joint on that side of the spine. The same speed relationship is found in the rearward movement of the pelvic carriages 20, 22 with the roller carriage 24. The movement of the pelvic carriages 20, 22 and rollers 26, 28 in this arrangement effectuates normal alignment of the lumbosacral spine.

As seen in FIG. 6 rollers 26 and 28 may be positioned at various locations with respect to the center line 92 on the roller carriage 24 in order to effectuate proper manipulation for different conditions. As illustrated in FIG. 6 the roller 26 is positioned at a similar location to that of roller 26 in FIG. 5. Roller 28 is positioned on the same side of the center line 92 as roller 26 in a position to ride along the muscle mass adjacent the spine on the same side of the spinal center line 92.

In FIG. 7 is illustrated a further variation in manipulation from that shown in FIGS. 5 or 6. It is contemplated that the sliding frame 90 has been adjusted so as to cause an opposite initial movement of the pelvic carriages 20 and 22 from that in FIGS. 5 and 6 such that pelvic carriage 22 moves initially rearward in direction. The linkage as illustrated in FIG. 7 causes the roller carriage 24 to also move in a rearward direction. The first roller 28 is shown to be adjacent to the center line 92 and rearward of the second roller 26 on the opposite side of the center line 92. The roller 28 is positioned within the groove between the muscle mass and the center line 92 of the spinal column. The second roller 26 is positioned similar to roller 28 in FIG. 6 and rides along the muscle mass adjacent to the spine. This relative relationship may also be utilized to effectuate certain types of manipulation as desired.

It is desired that the manipulation of the present invention be performed without twisting of the joints of the spine as well as effectuating the reciprocating motion of the body portions in a desired manner. The present invention is specifically directed to certain portions of the lower back so as to effectuate proper manipulation and realignment of the joints therein for the restoration of normal and pain free movement.

The present invention may be embodied in other specific forms without departing from the spirit or essential attributes thereof and, accordingly, reference should be made to the appended claims, rather than to the foregoing specification, as indicating the scope of the invention.

I claim:

1. An apparatus for manipulation of the lower back comprising: two pelvic carriages each positioned adjacent one another and adapted to support opposite sides of the rear of the pelvis, a roller carriage having two rollers adapted for contacting the lower back adjacent the center line of the spine when the pelvic carriages are supporting the pelvis, means for causing a reciprocating movement of the pelvic carriages with respect to one another in opposite directions, means for simultaneously causing a reciprocating motion of the roller carriage in a timed relationship with respect to the movement of the pelvic carriages with the rollers adapted to contact and move along the lumbosacral portions of the spine during reciprocation.

2. An apparatus as claimed in claim 1 wherein the initial movement of the pelvic carriage adapted to support the right side of the pelvis is in a footward direction during reciprocation.

3. An apparatus as claimed in claim 1 wherein the initial movement of the pelvic cariage adapted to support the right side of the pelvis is in a headward direction during reciprocation.

4. An apparatus as claimed in either claim 2 or 3 wherein the initial movement of the roller carriage is in a footward direction during reciprocation.

5. An apparatus as claimed in claim 4 wherein one roller is adapted to contact the portion of the back directly adjacent the center line of the spinal column on one side, and the second roller is adapted to contact the muscle mass adjacent the spinal column on the lower back.

6. An apparatus as claimed in claim 5 wherein the second mentioned roller is adapted to contact the muscle mass adjacent the spinal column on the opposite side of the center line of the spine from the contact of the first roller.

7. An apparatus as claimed in claim 6 wherein means for causing the reciprocating motion of the roller carriage is adapted to move the first mentioned roller to contact the back at a position medially past or to the inside of the ilium or hip and strike the posterior aspect of the sacrum on one side of the center line of the spine.

8. An apparatus as claimed in claim 7 wherein the second mentioned roller is positioned relatively headward of the first mentioned roller and farther from the center line of the spine than the first mentioned roller such that it does not strike the sacrum.

9. An apparatus as claimed in claim 8 wherein the reciprocating motion of the roller carriage is at a speed twice that of the speed of the pelvic carriage motion.

10. An apparatus as claimed in claim 5 wherein the second mentioned roller is adapted to contact the muscle mass adjacent the spinal column on the same side of the center line of the spine as the contact of the first roller.

11. An apparatus as claimed in claim 7 wherein said means for causing the reciprocating motion of the roller carriage is adapted to move the first mentioned roller to contact the back at a position medially past or to the inside of the ilium or hip and strike the posterior aspect of the sacrum on one side of the center line of the spine.

12. An apparatus as claimed in claim 11 wherein the second mentioned roller is positioned relatively headward of the first mentioned roller and farther from the center line of the spine than the first mentioned roller such that it does not strike the sacrum.

13. An apparatus as claimed in claim 12 wherein the reciprocating motion of the roller carriage is at a speed twice that of the speed of the pelvic carriage motion.

14. A method of exercising and manipulating the body comprising the steps of: separately contacting and supporting the opposite sides of the pelvis; moving the pelvis on opposite sides in an opposited reciprocating motion; further separately contacting the lumbosacral spine at two defined positions; moving the spinal contacts sequentially and substantially continuously along two lines parallel with the center line of the spine; and sumultaneously reciprocating the spinal contact movement in a timed relationship with the receprocating motion of the two sides of the pelvis.

15. The method according to claim 14 wherein moving the pelvis contacts is such that each side moves in one direction and returns to the neutral side-by-side position, the reciprocating motion never proceeding beyond the neutral position in a direction opposite the initial direction of motion of the contact.

* * * * *